US00PP09804P

United States Patent [19]

Holmes

[11] Patent Number: Plant 9,804

[45] Date of Patent: Feb. 11, 1997

[54] 'ALA' ST. AUGUSTINEGRASS

[75] Inventor: James M. Holmes, McHenry County, Ill.

[73] Assignee: Warren's Turf Group, Inc., South Bay, Fla.

[21] Appl. No.: 512,277

[22] Filed: Aug. 8, 1995

[51] Int. Cl.[6] ..... A01H 5/00

[52] U.S. Cl. ..... Plt./90.1

[58] Field of Search ..... Plt./90.1

[56] References Cited

U.S. PATENT DOCUMENTS

| | | | |
|---|---|---|---|
| P.P. 2,863 | 2/1969 | Long | Plt./90.1 |
| P.P. 2,864 | 2/1969 | Long | Plt./90.1 |
| P.P. 3,180 | 5/1972 | Gruis et al. | Plt./90.1 |
| P.P. 3,491 | 2/1974 | Garrett et al. | Plt./90.1 |
| P.P. 3,681 | 2/1975 | Gruis et al. | Plt./90.1 |
| P.P. 3,698 | 4/1975 | Gruis et al. | Plt./90.1 |
| P.P. 3,834 | 3/1976 | Garrett | Plt./90.1 |
| P.P. 4,097 | 9/1977 | Gruis et al. | Plt./90.1 |
| P.P. 6,126 | 3/1988 | Riordan | Plt./90.1 |
| P.P. 6,372 | 11/1988 | Mixson et al. | Plt./90.1 |
| P.P. 6,921 | 7/1989 | Mixson et al. | Plt./90.1 |
| P.P. 6,922 | 7/1989 | Mixson et al. | Plt./90.1 |
| P.P. 7,699 | 10/1991 | Busey | Plt./90.1 |
| P.P. 7,852 | 4/1992 | Busey | Plt./90.1 |
| P.P. 9,395 | 12/1995 | Kirkland et al. | Plt./90.1 |

*Primary Examiner*—James R. Feyrer

*Attorney, Agent, or Firm*—Klarquist Sparkman Campbell Leigh & Whinston, LLP

[57] ABSTRACT

An asexually reproduced variety of perennial St. Augustinegrass with a unique combination of characters including white stigmas, yellow anthers, an absence of leaf hairs, floret number per raceme, raceme length, leaf length, and internode length, having good turf performance, good winter hardiness, and a distinct DNA fingerprint.

2 Drawing Sheets

BACKGROUND OF THE INVENTION

This invention relates to a new and distinct perennial St. Augustinegrass cultivar, tested as Ala, that was discovered by the inventor in a home lawn in Glenwood, Ala. It was identified as a clone superior in quality and density from the surrounding common St. Augustinegrass. Ala was asexually propagated by cutting of stolons, rooting them, and moving Ala to Buckholts, Tex. for further study. Ala is a high quality, stoloniferous turf with moderate winter hardiness for use as a lawn or turf wherever St. Augustinegrass is adapted, with winter survival in the northern areas of St. Augustinegrass adaptation, such as Austin, Tex.

BRIEF DESCRIPTION OF THE ILLUSTRATIONS

FIG. 1 shows DNA fingerprints of St. Augustinegrass varieties. The DNA fingerprints were produced by polymerase chain reaction using random primers, illustrating Ala is different from Seville and Raleigh.

DETAILED DESCRIPTION OF THE PLANT

Figure 1:
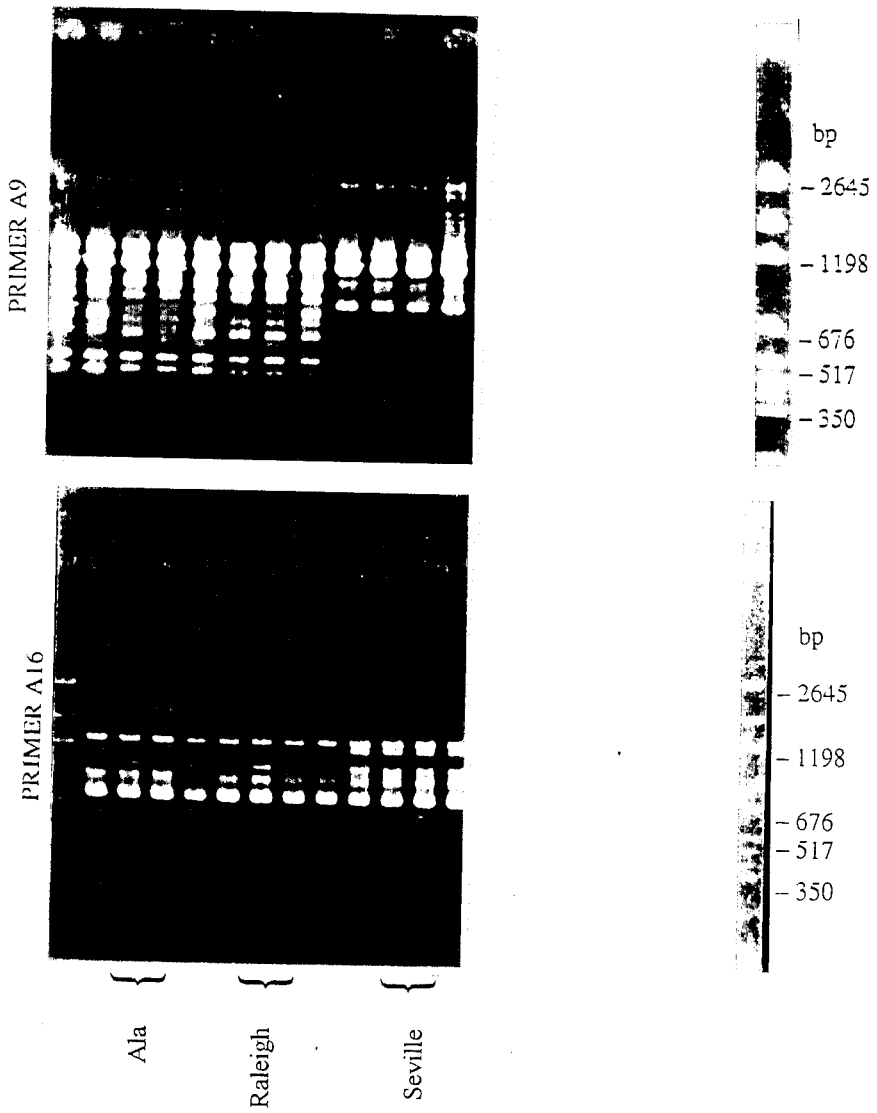
Figure 2:
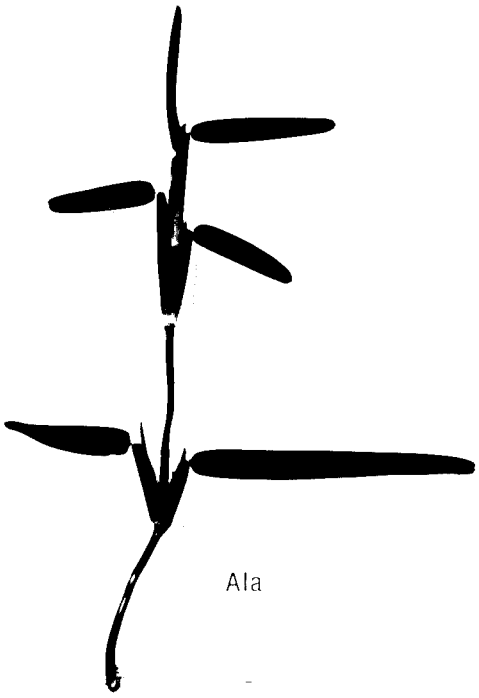
FIG. 2 is a photograph of a vegetative stolen of Ala.
Figure 3:
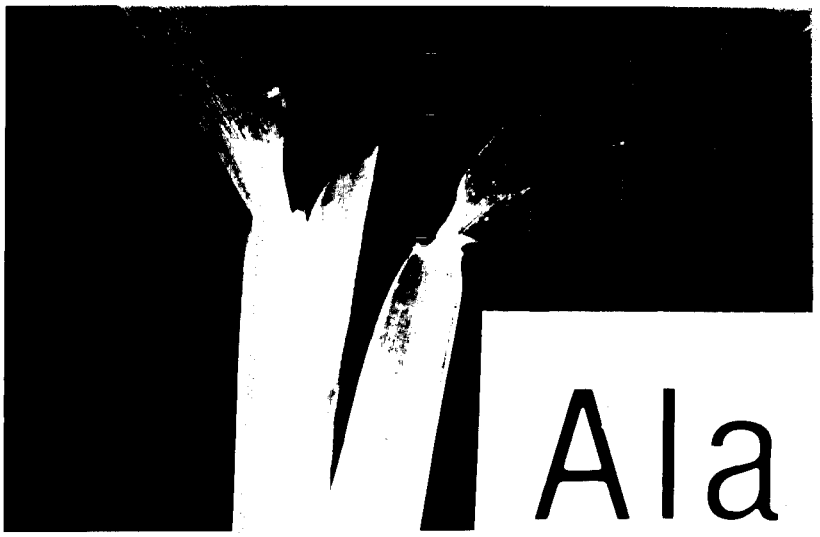
FIG. 3 is a photographof the leaf blade and ligule of Ala.

Ala was characterized in greenhouse and field conditions. Ala is a unique variety of St. Augustinegrass [*Stenotaphrum secundatum* (Walt.) Kuntze] discovered under cultivated, mowed turf conditions at the home lawn described above. Ala was identified as higher in density and quality from the surrounding common St. Augustinegrass. Ala was propagated by cutting of stolons, rooting them in soil, and planting of the rooted stolons to provide planting stock for studying performance and for comparisons with commercial varieties. Ala remained stable in both performance and morphological characters after propagation. Ala has been propagated by sod, plugs, and stolons. No seedling establishment from Ala has been noticed in either greenhouse or field plantings, suggesting lack of sexual reproduction.

Ala is distinguished from other varieties of St. Augustinegrass by the combination of characters of white stigmas, yellow anthers, floret number per raceme, raceme length, leaf length, internode length, and lack of leaf hairs. Ala shows a distinct DNA fingerprint. Ala is closest in appearance and performance to Raleigh St. Augustinegrass.

The creeping stolons of Ala are dorsiventrally compressed and root adventitiously at the nodes. Ala lacks rhizomes. Color notations of plant tissues were based on the Munsell Color Charts for Plant Tissues, Munsell Color, Baltimore, Md., 1977. Color notations are affected by light quality and fertility and general growth of the plants. Ala has a distinct lack of purple color in the stolons, in contrast to many St. Augustinegrasses. Leaf blades of Ala are folded in the bud, contracted at the base, and obtuse at the tip. There is an absence of hairs on the leaf blades of Ala. Measured under greenhouse conditions in July 1994, the genetic, adaxial leaf color of Ala is 7.5 GY 5.4, with Raleigh having a color of 5 GY 5/8.

The ligule of Ala is a line of short hairs, approximately 2 mm in length. The leaf sheaths are laterally compressed and are approximately 38.6 mm in length (Table 1), shorter than Raleigh at a mean of 40.9.

The flag leaf width of Ala is 6.4 mm, with Raleigh having a mean of 8.0 mm (Table 2). Ala has white stigmas and yellow anthers, undistinguished in color from other plants of the species (Table 3). The floral region of Ala consists of spikelets partially embedded in a flattened and thickened rachis of a short, unilateral spicate inflorescence with a raceme length of 57 to 71 mm (Table 4). Ala has a mean of 25 florets per raceme, which trends to be a lower number of spikelets than Raleigh, and more than Seville (Table 4). The mean spikelet length of Ala is 3.89 mm, with Raleigh having a mean of 4.23, measured under the same growth conditions. The spikelets of Ala are awnless. The dates of flowering are similar to that of Raleigh.

The mean stolon internode diameter of Ala is 2.38×2.97 mm, less than Raleigh with a stolon diameter of 3.1×3.5 mm. Ala has a mean internode length of 4.8 cm (Table 5), shorter than Raleigh with a mean of 7.8 cm, and longer than Seville with a mean of 4.2 cm. The shorter internode length of Ala compared to Raleigh contributes to a tight turf canopy and high quality. Ala is vigorous in growth, and spreads by leafy stolons with formation of tight turf by tiller production. Ala readily develops adventitious roots, an advantage in vegetative propagation. The rooting depth of Ala appears to be average, without observation of the extremely deep rooting character of some St. Augustinegrasses.

The chromosome number of Ala is 18.

Quality in turf performance may be defined as a combination of characters of color, density, uniformity, and leaf texture. Density is defined as the number of leaves and tillers per unit area. Uniformity is defined as freedom from weeds or diseases. Ala shows high quality turf performance in field trials in Buckholts, Tex., Ala showed quality as a fine leaf texture of 7.0 mm on the second youngest leaf, compared to Raleigh with a leaf texture of 7.2 mm. Ala has good turf performance when mowed at 5 cm mowing height, with a rotary mower. Ala is vigorous in establishing a turf cover, as indicated in the growth from a 7.5% cover to 52.5% in an approximate 6 month period (Table 6). Ala expresses high vigor in tiller density, forming a dense and uniform turf, competitive against weed invasion. Ala is intermediate in rate of greenup, having a mean of 7.5% on Apr. 22, 1994, with Raleigh showing 17.5% and Seville 3.3% on the same date in Buckholts, Tex. Ala was intermediate in entering winter dormancy, earlier than Seville, and similar to Raleigh at Buckholts, Tex.

The high quality performance of Ala may be directly related to the high tiller density which competes with weeds, and the superior winter hardiness (tested as survival in Buckholts, Tex.). Ala has shown good drought resistance with continued growth as unirrigated turf adjacent to Texas Common St. Augustinegrass in Buckholts, Tex. Ala illustrated no excessive thatching tendencies when maintained as turf as observed in Buckholts, Tex., and in the original collection site, Glenwood, Ala. Ala has shown moderate susceptibility to gray leaf spot and brown patch in the Buckholts, Tex. The shade tolerance of Ala has not been tested. The chinch bug and other insect resistances of Ala have not been tested in replicated trials; however, no insect problems were observed in the test areas.

With the presence of white stigmas, yellow anthers, and an absence of leaf hairs, Ala is distinguished from all patented St. Augustinegrasses except #141, 6-72-99 (Delmar), and 6-72-182 (Table 3, 3a). Ala exhibits more florets per raceme than Seville (Table 4), is not different from number of florets per raceme than Raleigh, but has a shorter raceme length than Raleigh. Ala has a flag leaf sheath longer than Seville (Table 1); Seville has a flag leaf sheath longer than 6-72-182 (U.S. Plant Pat. No. 6,922). Ala has a raceme averaging 65.1 mm (Table 4). Delmar has a spike 93 mm in length (U.S. Plant Pat. No. 6,372), with #141 having an average length of 8.97 cm (U.S. Plant Pat. No. 3,834), both longer than Ala. Ala has longer internodes (Table 5) than #141 (U.S. Plant Pat. No. 3,834). In turf evaluations, Ala exhibited a density rating not different from Seville or Raleigh (Tables 6). Ala shows a distinctly different DNA from Seville and Raleigh using PCR DNA fingerprints (FIG. 1).

DETAILED SUMMARY OF DNA FINGERPRINT ANALYSIS

Dr. Lin Wu, Univ. California — Davis, performed the DNA fingerprint analysis. The St. Augustinegrass DNA fingerprints were Ala, Seville, and Raleigh. The DNA fingerprints were produced by polymerase chain reaction using random primers. The four DNA fingerprint profiles of each variety produced by the primers A9 and A16 from the left to right are the DNA profiles of the two duplicate DNA extractions extracted from the leaf tissue of the vegetatively propagated clones. The results of the DNA fingerprint analysis are summarized:

1. Ala is different from Raleigh by Primer A9 and A16.
2. Ala is different from Seville by Primer A9 and A16.

TABLE 1

Morphological comparisons of Ala and commercial St. Augustinegrass varieties measured from plants maintained in greenhouse pots

| Variety | Sheath Length[1] mm | Sheath Length[2] mm | Sheath Length[3] mm | Leaf Width[3] mm |
|---|---|---|---|---|
| Ala | 50.4a | 38.7a | 26.8a | 7.6c |
| Raleigh | 52.9a | 36.3a | 33.6a | 8.9a |
| Seville | 35.2b | 22.4c | 17.6c | 5.8c |

[1]Measured on flag leaf sheaths, Sept. 1993; Mean separation by General Linear Models.
[2]Measured on flag leaf sheaths, Oct. 1994; Mean separation by Waller/Duncan tests.
[3]Measured on third youngest leaf, Spet. 1993; Mean separation by Waller/Duncan tests.

TABLE 2

Comparisons of Ala and other St. Augustinegrass flag leaf widths and lengths

| Variety | Flag Leaf Width[1] mm | Flag Leaf Width[2] mm | Flag Leaf Length[3] mm |
|---|---|---|---|
| Ala | 7.1a | 5.7b | 21.2a |
| Raleigh | 7.9a | 8.1a | 19.8a |
| Seville | 5.9b | 5.1b | 9.9b |

[1]Measured July 1994 on greenhouse planted material with mean separation by Waller/Duncan tests.
[2]Measured Oct. 1994 on greenhouse planted material with mean separation by Waller/Duncan tests.
[3]Measured Oct. 1994 on greenhouse planted material with mean separation by Waller/Duncan test.

TABLE 3

Stigma color, anther color, and presence of leaf hairs on St. Augustinegrass varieties from plants maintained in greenhouse pots, July 1994

| Variety | Stigma Color | Anther Color | Leaf Hairs |
|---|---|---|---|
| Ala | white | yellow | absent |
| Raleigh | white | yellow | absent |
| Seville | purple | yellow | absent |

TABLE 3a

Stigma color, anther color, and leaf hairs of St. Augustinegrasses as listed in U.S. Plant Patents

| Variety | Stigma Color | Anther Color | Leaf Hairs | US Pat. No. |
|---|---|---|---|---|
| Ea 611081 | Purple | • | • | 2,863 |
| Ea 6416 | Purple | • | • | 2,864 |
| Ea 673 | Purple | • | • | 3,180 |

TABLE 3a-continued

Stigma color, anther color, and leaf hairs of St. Augustinegrasses as listed in U.S. Plant Patents

| Variety | Stigma Color | Anther Color | Leaf Hairs | US Pat. No. |
|---|---|---|---|---|
| #4875 | Purple* | • | • | 3,491 |
| 73176 | Purple | • | • | 3,681 |
| 45176 | Purple | • | • | 3,698 |
| #141 | White | • | • | 3,834 |
| 615866 (Seville) | Purple | • | • | 4,097 |
| PS-247 | Purple | Light purple | • | 6,126 |
| 6-72-99 (Delmar) | White | Yellow | • | 6,372 |
| 6-72-182 | White | Yellow | • | 6,921 |
| 6-72-130 | Purple | Purple | • | 6,922 |
| FX-33 | Purple | Orange Yellow | Many Present | 7,699 |
| FX-10 | 5RP 3/10 | 10YR 7/10 | | 7,852 |

*With white filaments

TABLE 4

Morphological comparisons of Ala and other commercial St. Augustinegrass varieties measured from plants maintained in greenhouse pots

| Variety | Floret[1] # | Floret[2] # | Floret[3] # |
|---|---|---|---|
| Ala | 29.4a | 28.2ab | 17.6ab |
| Raleigh | 34.2a | 30.1a | 19.2a |
| Seville | 24.1b | 23.7b | 13.0b |

| Variety | Raceme Length[1] mm | Raceme Length[2] mm | Raceme Length[3] mm |
|---|---|---|---|
| Ala | 70.5b | 67.8b | 57.1a |
| Raleigh | 93.3a | 76.5a | 59.6a |
| Seville | 67.8b | 61.3c | 41.7b |

[1]Measured Sept. 1993; mean separation by General Linear Models.
[2]Measured July 1994; mean separation by Waller/Duncan tests.
[3]Measured October 1994; mean separation by Waller/Duncan tests.

TABLE 5

Stolon internode lengths of Ala and commercial St. Augustinegrass varieties measured from plants maintained in greenhouse pots

| Variety | Internode 2–3 | Internode 3–4 |
|---|---|---|
| Ala | 4.7c[1] | 4.9c |
| Raleigh | 8.1a | 7.5a |
| Seville | 4.1c | 4.2c |

[1]Measured 2 October 1994 with mean separation by Waller/Duncan tests.

TABLE 6

Percent plot cover and density ratings of Ala and other commercial St. Augustinegrass varieties established July 1993 from plugs in replicated trials at Buckholts, Texas. Percent cover relates to winter survival as measured on 22 April 1994

| | Date | | |
|---|---|---|---|
| Variety | 22 Apr 94 % Cover | 17 Oct 94 % Cover | 17 Oct 94 Density Rating |
| Ala | 7.5b[1] | 52.5a[1] | 4.5a[2] |
| Raleigh | 17.5a | 80.0a | 5.5a |
| Seville | 3.3b | 52.5a | 4.0a |
| Tx. Comm. | 1.3b | 3.0b | 0.3b |

[1]Mean separation by Waller/Duncan.
[2]Ratings made on a scale of 1–9 with 9 = most dense, with mean separation by Waller/Duncan.

I claim:

1. A new and distinct cultivar of an asexually reproduced St. Augustinegrass plant substantially as herein shown and described, with a unique combination of characters including white stigmas, yellow anthers, an absence of leaf hairs, floret number per raceme, raceme length, internode length, having good turf performance, good winter hardiness, and a distinct DNA fingerprint.

* * * * *